ium salts are useful as metal corrosion inhibitors, and espe-
United States Patent
Chiang

[19]

[11] Patent Number: 4,880,907
[45] Date of Patent: Nov. 14, 1989

[54] QUATERNARY SALTS OF QUINOLINE OLIGOMER AS METAL SURFACE PROTECTIVE MATERIALS (C-2212)

[75] Inventor: Long Y. Chiang, Somerset, N.J.
[73] Assignee: Exxon Research and Engineering Company, Florham Park, N.J.
[21] Appl. No.: 155,225
[22] Filed: Feb. 12, 1988

Related U.S. Application Data

[63] Continuation-in-part of Ser. No. 887,364, Jul. 17, 1986, Pat. No. 4,727,185.

[51] Int. Cl.$^4$ ............................................. C08G 73/06
[52] U.S. Cl. .................................. 528/423; 252/390; 252/391; 252/392; 252/394; 252/389.1; 252/389.22; 524/612
[58] Field of Search ................. 528/423; 252/390, 391, 252/392, 394, 389.1, 389.22; 524/612

[56] References Cited

U.S. PATENT DOCUMENTS

| | | | |
|---|---|---|---|
| 2,955,093 | 10/1960 | Solomon | 260/23.7 |
| 3,178,376 | 4/1965 | Cook | 260/2 |
| 4,028,268 | 6/1977 | Sullivan, 3rd et al. | 252/8.55 C |
| 4,275,191 | 6/1981 | Quinlan | 528/423 |
| 4,312,832 | 1/1982 | Quinlan | 528/423 |
| 4,341,657 | 7/1982 | Quinlan | 528/423 |
| 4,387,041 | 6/1983 | Hort et al. | 252/392 |
| 4,676,834 | 6/1987 | Treybig | 106/14.15 |
| 4,727,135 | 2/1988 | Chiang et al. | 528/423 |

FOREIGN PATENT DOCUMENTS 1010247 11/1965 United Kingdom .

OTHER PUBLICATIONS

Stille, J. K., *Macromolecules*, 1981, pp. 870-880.

Primary Examiner—Harold D. Anderson
Assistant Examiner—T. Mosley
Attorney, Agent, or Firm—Joseph J. Dvorak

[57] ABSTRACT

Novel oligomeric quinolinium salts are disclosed. These are formed by reacting quinoline oligomers with alkylating agents such as benzyl halide, p-α-xylenyl dihalide and alkyl sulfates. The novel oligomeric quinolinium salts are useful as metal corrosion inhibitors, and especially as aqueous acid corrosion inhibitors. The novel compounds are represented by the formulae:

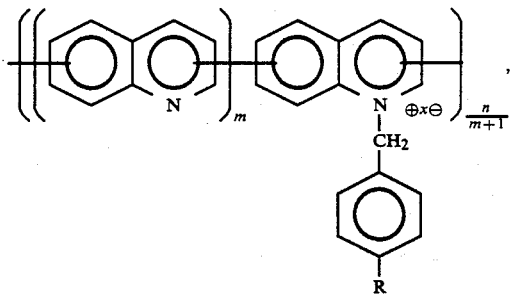

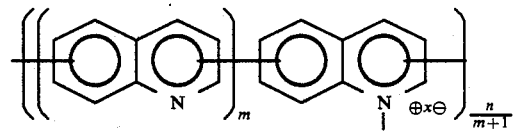

and

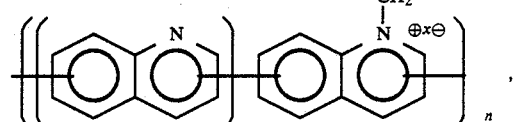

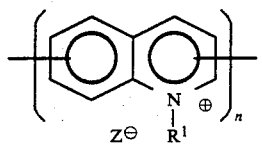

wherein n and m are integers, with n being greater than 2 and up to about 200 and m being equal to or greater than 1, R is H or an alkyl group having from 1 to about 20 carbon atoms, $R^1$ is an alkyl group having 1 to about 20 carbon atoms, $X^-$ is a chloride, bromide or iodide and $Z^-$ is an anion selected from $BF_4^-$, $SO_4^=$, $ClO_4^-$, $PF_6^-$ and $HSO_4^-$.

14 Claims, No Drawings

QUATERNARY SALTS OF QUINOLINE OLIGOMER AS METAL SURFACE PROTECTIVE MATERIALS (C-2212)

CROSS REFERENCE TO RELATED APPLICATION

This application is a continuation-in-part application of copending Ser. No. 887,364, filed July 17, 1986 now U.S. Pat. No. 4,727,135.

FIELD OF THE INVENTION

The present invention is directed toward novel oligomeric quinolinium halides and the use of such compounds as metal corrosion inhibitors.

BACKGROUND OF THE INVENTION

The corrosion of metals by acids is a problem that is encountered in many industries. In the petroleum industry, for example, the corrosion of oil field tubular goods and similar equipment by hydrochloric acid solutions and other corrosive materials used in secondary oil recovery procedures and well stimulation operations has necessitated the use of inhibitors to protect corrosion of such goods and equipment against corrosion. Many different types of materials have been suggested in the past for use as corrosion inhibitors. In U.S. Pat. No. 4,028,268, for example, a multi-component inhibitor formulation is disclosed which includes certain specified quaternized cyclic nitrogen bases, specific acetylenic alcohols, a specific surface active agent and a formic acid derivative.

In U.S. Pat. No. 4,387,041, an aqueous composition for inhibiting corrosion of metals is disclosed which comprises an acid and, as a corrosion inhibitor, 3-dialkylamino-3-(substituted phenyl)-prop-1-yne.

U.S. Pat. No. 4,341,657, polymers derived from quinolines and pyridine compounds are disclosed as being useful as metal corrosion inhibitors. The polymers are referred to in the references as being polyquinolines and polypyridines, but they do not have a repeating quinoline or pyridine moiety in their respective structures.

In U.S. Pat. No. 4,676,834, there are disclosed novel compositions for use as corrosion inhibitors in servicing of oil and gas wells. Such compositions include the reaction product of quinoline, for example, with a cycloaliphatic mono-aldehyde.

Notwithstanding the teachings of the foregoing references, there has been a continuing search for new materials which are effective in inhibiting corrosion, particularly inhibiting corrosion of metals in highly acid solutions and which have a relatively high thermal stability so that they can be employed, for example, in deep drilling operations and other high temperature, corrosive environments.

In copending application Ser. No. 887,364, filed July 17, 1986 now U.S. Pat. No. 4,727,135 and incorporated herein by reference, there is disclosed a catalytic dehydrogenation process for preparing quinoline oligomers.

SUMMARY OF THE INVENTION

Simply stated, the present invention is predicated on the discovery that quinoline oligomers, i.e. oligomers having recurring polyquinoline moieties, represented by the formula:

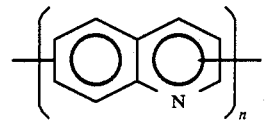

wherein n is an integer greater than 2, react with alkylating agents such as p-alkylbenzyl halide, p-α-dihaloxylene, dialkylsulfate and the like, to form novel quaternary polyquinolinium salts that are particularly useful as corrosion inhibitors. Thus, one aspect of the present invention comprehends novel quaternary quinolinium salts represented by the formulae:

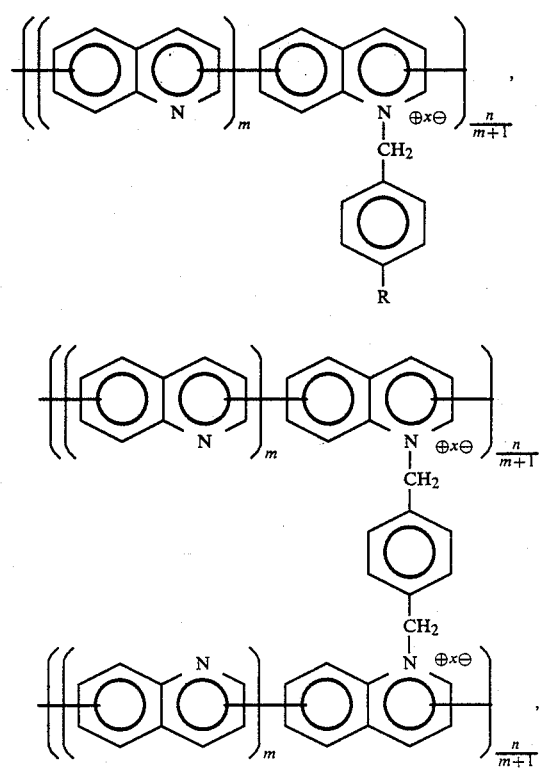

and

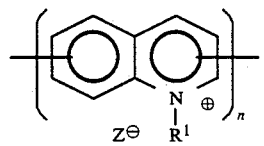

wherein n and m are integers, with n being greater than 2 and up to about 200 and m being equal to or greater than 1 and up to about 100. Also, R is hydrogen or an alkyl group having from 1 to about 20 carbon atoms and $R^l$ is an alkyl group having from 1 to about 20 carbon atoms. In the above formulae x is a halide ion such as chloride, bromide and iodine ion and Z is an anion such as $SO_4^=$, $ClO_4^-$, $BF_4^-$, $I^-$, $PF_6^-$, and $HSO_4^-$.

In yet another embodiment of the present invention, there is provided a new composition particularly suitable for corrosion inhibition of metals which comprises a corrosion inhibiting amount of quaternary ammonium salts of polyquinoline oligomers formed by reacting a polyquinoline oligomer or mixture thereof of the formula:

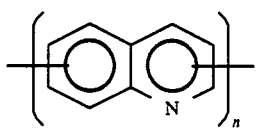

wherein n is from 2 to about 200 with an alkylating agent selected alkyl and benzyl compounds such as:

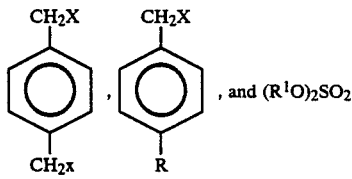

wherein x is Cl, Br or I and R is H or an alkyl group having 1 to about 20 carbon atoms and $R^1$ is an alkyl group having 1 to about 20 carbon atoms and dialkoxy carbonium salts and trialkyl oxonium salts such as the dimethoxy and diethoxy carbonium boron tetrafluorides and trimethyl and triethyl oxonium boron tetrafluorides.

In yet another embodiment of the present invention, there is provided a method of preparing novel quaternary derivatives of polyquinoline oligomers having the formula:

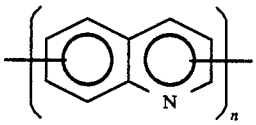

wherein the valence bond may be attached at any ring position and n is any integer greater than 2, by reacting such polyquinoline oligomers with an alkylating agent selected from benzyl halides and alkyl sulfates having the formula:

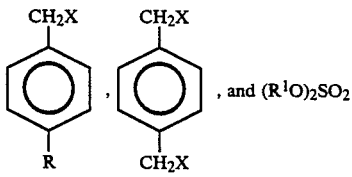

wherein R is H or an alkyl group having 1 to about 20 carbon atoms and $R^1$ is an alkyl group having from 1 to about 20 carbon atoms and dialkoxy carbonium salts and trialkyl oxonium salts.

These and other embodiments of the present invention will be better understood upon reading the "Detailed Description", which follows.

DETAILED DESCRIPTION OF THE INVENTION

The catalytic dehydrogenative polymerization of 1,2,3,4-tetrahydroquinoline using rhenium sulfide as a catalyst proceeds as shown in Equation 1:

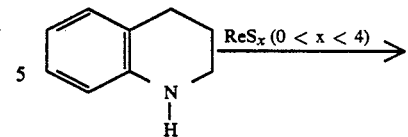

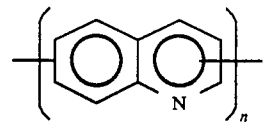

Basically, commercial grade 1,2,3,4-tetrahydroquinoline can be used to form the quinoline oligomers without further purification.

In general, in preparing the quinoline oligomers the preferred rhenium sulfide catalyst is an amorphous powder having a surface area of about 0.02 to about 30 $m^2/g$. These catalysts typically are prepared by the reaction of ammonium perrhenate or rhenium (v) chloride with hydrogen sulfide or lithium sulfide. An alternate method for preparing a suitable rhenium sulfide catalyst is described in U.S. Pat. No. 4,308,171 and incorporated herein by reference.

The crude reaction product obtained in the foregoing process is separated from catalyst, where necessary, and purified by solvent extraction techniques such as that described in the Examples herein.

The molecular weight distribution of the resulting oligomer obtained in accordance with the foregoing method tends to vary from batch to batch, depending upon the reaction conditions such as temperature and pressure, and the procedures employed for separating reaction product. Therefore, to insure consistency in the various experiments pursued in developing the corrosion compositions of the present invention, a fraction of the oligomer which was soluble in acetic acid and insoluble in a diethylether-chloroform mixture having a ratio of 3 volumes of diethylether to 1 volume of chloroform was used, and this fraction was characterized by its $^1$H-NMR spectrum and found to consist of quinoline oligomers with an average repeating quinoline unit of 6. It should be readily appreciated, however, that while, for test purposes, it was preferred to use a polyquinoline oligomer having the repeating quinoline unit of 6, in general, quinoline oligomers having repeating units in the range of from about 2 to about 200, and preferably from about 5 to 13, are quite suitable in the practice of the present invention.

The quinoline oligomers are converted to the novel quaternary ammonium compounds by interaction with alkylating agents, especially p-alkylbenzyl halides, dihaloxylenes, dialkyl sulfates, dialkoxy carbonium salts and trialkyloxonium salts such as:

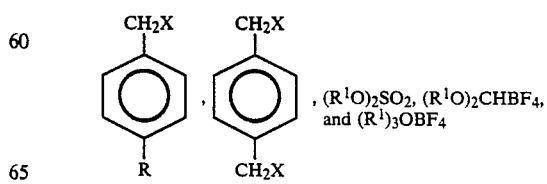

wherein X is Cl, Br, or I and R is hydrogen or alkyl group having from 1 to about 20 carbon atoms and $R^1$ is an alkyl group having from 1 to about 20 carbon atoms.

For example, various quaternary salts of quinoline oligomer can be formed by the alkylation reaction of the quinoline oligomer with benzyl halide and para-substituted benzyl halide in a suitable solvent at temperatures in the range of about 25° C. to 150° C., and preferably at about 90° C. The reaction is illustrated in Equation 2:

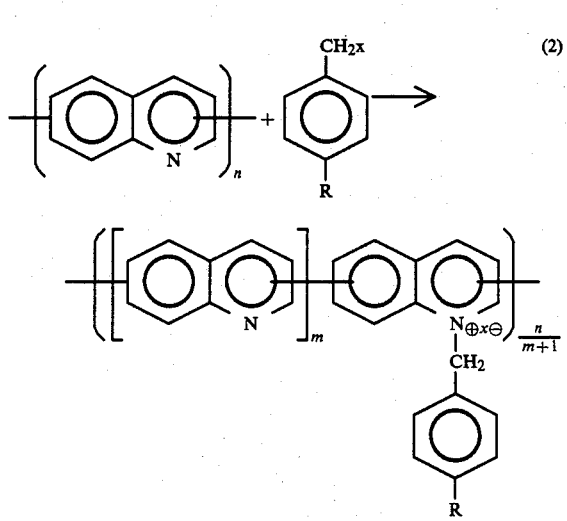
(2)

Any organic material which is not reactive toward the oligomer and to the benzyl halide may be employed as a solvent in carrying out this reaction. Among those solvents found to be suitable are toluene, chloroform and dimethyl sulfoxide.

Generally the reaction is conducted using a slight excess of the benzyl halide.

As is shown in Equation 2, the quinoline oligomer is not totally quaternized, apparently due to the steric effect between the quinoline moieties. Nonetheless, it has been found that up to 50 percent of the quinoline moieties can be quaternized.

In an alternate embodiment of the present invention, the polyquinoline chains can be quaternized to form a double quaternary salt by reacting the quinoline oligomer with a dialkyl aryl halide such as p-α-dihaloxylene. This reaction is illustrated in Equation 3 below:

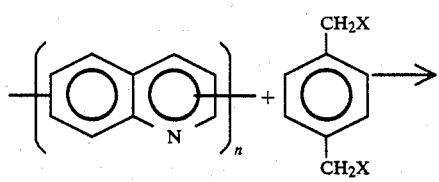
(3)

-continued

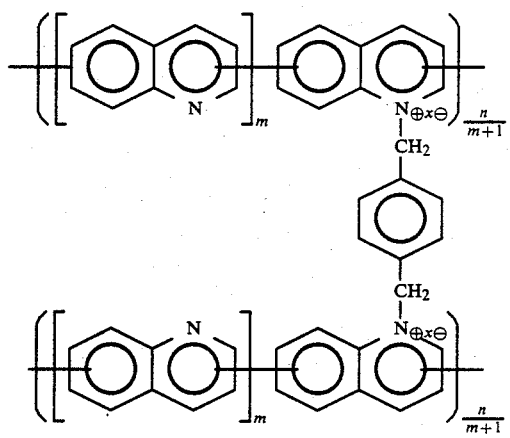

Basically, the same types of solvents and temperature conditions can be used in carrying out this reaction. In general, however, in this instance an excess of the quinoline oligomer is used.

In yet other embodiments of the present invention, the quinoline oligomer is quaternized by reaction with a dialkyl sulfate as illustrated by Equation 4; and alternatively by dialkyoxy carbonium salt or a trialky oxonium salt, such as a boron tetrafluoride salt, as shown in Equations 5 and 6, respectively:

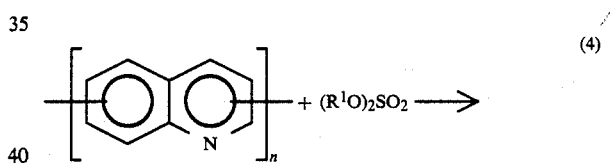
(4)

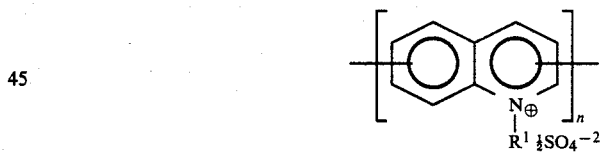
(5)

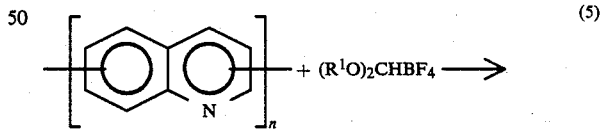
(6)

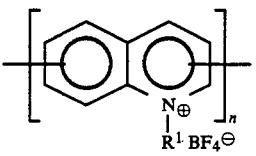

Similar solvents and temperature conditions mentioned above are employed. Also, in this instance, a slight excess of the alkylating agent is used.

The anion in the alkyl oligomeric quinoline salt obtained as described above can be exchanged for another anion by reaction with an appropriate counter salt. For example, methyl quinolinium sulfate is water soluble. Addition of tetrabutyl ammonium perchlorate to an aqueous solution of methyl quinoline sulfate results in precipitation of methyl quinolinium tetrafluoroborate.

The quaternary ammonium salts prepared in accordance with the practice of the present invention were identified by various spectroscopic methods ($^1$H-NMR, $^{13}$C-NMR, IR, and mass spectroscopy) and by elemental analyses.

The degree of quaternization that is achieved can be estimated, at least in principle, from the ratio of peak intensity between the benzyl proton signal at 6.5 to 6.9 ppm and the rest of the aromatic proton signals at 7.4 to 11.0 ppm ($^1$H-NMR). This technique, in fact, was employed, although the results obtained tended to be a little bit lower than the value obtained from elemental analyses.

The novel quaternary compounds of the present invention can be employed, especially in aqueous solutions, as novel corrosion inhibiting compositions. The concentration of the quaternary ammonium salt used in the aqueous solution will, of course, vary over a wide range. Suffice it to say that an effective amount of the quaternary ammonium compound employed as a corrosion inhibitor is an effective amount. In any particular application the corrosion inhibiting amount will depend, of course, upon the nature of the metal to be protected against corrosion, the corrosive acid, the acid concentration, the temperature and similar variables. In general, however, it has been found that the corrosion inhibitor composition of the present invention is effective when used in amounts ranging from about 0.01 to about 4 weight percent, and preferably between about 0.05 and 2 weight percent based on the total weight of inhibitor and aqueous acid solution.

The present invention is further illustrated by the following examples:

EXAMPLE 1

Synthesis of Quinoline Oligomer

The quinoline oligomer used in the following examples was prepared according to the following procedure: A single neck round bottom flask equipped with condenser and an inert gas bubbler was charged with 200 g of 1,2,3,4-tetrahydroquinoline and 5 g of rhenium sulfide catalyst. The mixture was maintained under an argon atmosphere and heated in a heating mantle at 200° C. for 6 hours, and then at 270° C. for 1 week. At the end of the reaction, the resulting mixture was cooled to room temperature to give a dark solid. The product was isolated from the catalyst particles by Soxhlet extraction using glacial acetic acid (800 ml) as a solvent. The acetic acid solution was then concentrated to less than 100 ml by solvent evaporation under vacuum at 80° C., then added to 2 liters of water to cause precipitation of an orange semi-solid. The orange semi-solid was filtered and washed by water in a dilute (1N) sodium hydroxide solution. The solid was then stirred in 500 ml of methanol for 2 days. The resultant insoluble yellow solid which was filtered and washed with methanol to yield a first fraction amounting to 60 g. The methanol filtrates were then concentrated and added to 500 ml of diethylether, resulting in precipitation of a solid. This solid was separated by filtration and washed with ether to yield 40 g of a yellow solid. These two fractions were then combined and washed with a solution of chloroform and ether in the volume ratio of 1 to 3 to provide the quinoline oligomer used in the subsequent examples.

EXAMPLES 2 TO 5

These examples illustrate the synthesis of benzyl quinolinium bromide oligomers (BQO) in accordance with the practice of the present invention. In these reactions, a 1 neck round bottom flask was connected with a condenser and charged with 100 ml of solvent, 6.4 g of the quinoline oligomer prepared in accordance with Example 1, and 10.3 g of bromomethyl benzene. The solvent used in each experiment is set forth in Table 1. The mixture was stirred either at the refluxing temperature of the solvent or 90° C., whichever was lower, for at least 10 hours. The reaction mixture was then cooled to room temperature and added to 600 ml of diethylether to cause the precipitation of the product. The precipitates were separated by filtration, washed by ether and dried in vacuum to provide the oligomeric benzyl quinolinium bromides with the yields set forth in Table 1. Table 1 also shows under the column headed "Y" the fraction of the nitrogen atom of the quinolinium oligomer present that reacted with the quaternary ammonium salt.

TABLE 1

| Example | Solvent Used | Product Yield | Y |
| --- | --- | --- | --- |
| 2 | Toluene/Chloroform (1:1) | 65% | 0.43 |
| 3 | Toluene | 66% | 0.38 |
| 4 | Chloroform | 68% | 0.5 |
| 5 | Dimethylsulfoxide | 80% | 0.5 |

EXAMPLES 6 TO 9

These examples illustrate the synthesis of a cross-linked benzyl (p-α-xylenyl) quinolinium bromide oligomers (CBQO). In these examples, a 1 neck round bottom flask connected to a condenser was charged with 100 ml of a solvent, 6.4 g of the quinoline oligomer obtained in accordance with the procedure of Example 1, and 7.9 g of p-alphadibromoxylene. The reaction mixtures were stirred at either the refluxing temperature of the solvent or at 90° C., whichever temperature was lower, for at least 10 hours. The reaction mixture was then allowed to cool to room temperature and was added to 600 ml of diethylether to cause the precipitation of the product. The precipitates were filtered, washed with ether and dried in vacuum to give p-α-xylenyl quinolinium bromide oligomers as set forth in Table 2 below. Table 2 also sets forth the solvents employed in the experimental procedures, as well as the yields and the extent quaternization (Y) of the quinoline oligomer.

TABLE 2

| Example | Solvent Used | Product Yield | Y |
|---|---|---|---|
| 6 | Toluene/Chloroform (1:1) | 76% | 0.45 |
| 7 | Toluene | 80% | 0.35 |
| 8 | Chloroform | 75% | 0.5 |
| 9 | Dimethylsulfoxide | 95% | 0.5 |

EXAMPLE 10

This example illustrates the synthesis of methyl quinolinium sulfate oligomers (MQO). In the reaction, a 1 neck round bottom flask was connected with a condenser and charged with 100 ml of chloroform, 6.4 g of the quinoline oligomer prepared in accordance with Example 1, and 10 g of dimethyl sulfate. The mixture was stirred at the refluxing temperature of chloroform for at least 10 hours. The reaction mixture was then cooled to room temperature and added to 600 ml of diethylether to cause the precipitation of the product. The precipitates were separated by filtration, washed by ether and dried in vacuum to provide the oligomer methyl quinolinium sulfate with a 92% yield.

EXAMPLE 11

This example illustrates the procedure for establishing the corrosion inhibiting properties of the quaternary ammonium salts of the present invention. In these tests, two samples of steel were employed, namely cold rolled steel and stainless steel 304. In the general test procedure, the appropriate metal surface was polished with a metal cloth and then rinsed with distilled water and acetone prior to the test. For comparative purposes, of course, the cold rolled steel and the stainless steel 304 were tested for corrosion in the absence by treatment with the acid having the concentration shown in Table 3 below in the absence of the inhibitor. Thereafter the various metal surfaces were treated with the acid containing a specified amount of the inhibitor shown in the Tables below, the relative metal corrosion activity on the surfaces was interpreted in terms of metal weight loss during the test. Basically, as can be seen in Table 3, the compounds of the present invention are effective metal corrosion inhibitors in strongly acidic aqueous solutions.

TABLE 3

| Metal | Compound Used (% by weight) | Solution Medium | Time (days) | Weight Loss (mg/cm²/day) | % Protection |
|---|---|---|---|---|---|
| SS304 | None | Conc. HCl (12N) | 1 | 169.5 | |
| SS304 | BQO (0.3%) (Ex. 4) | Conc. HCl (12N) | 1 | 7.01 | 95.9 |
| SS304 | CBQO (0.3%) (Ex. 8) | Conc. HCl (12N) | 1 | 8.72 | 94.9 |
| SS304 | MQO (0.3%) (Ex. 10) | Conc. HCl (12N) | 1 | 14.60 | 91.4 |
| CRS | None | Aqueous HCL (6N) | 1 | 72.9 | |
| CRS | MQO (0.1%) (Ex. 10) | Aqueous HCL (6N) | 1 | 8.4 | 88.5 |
| CRS | BQO (0.1%) (Ex. 4) | Aqueous HCl (6N) | 1 | 23.3 | 68.0 |
| CRS | CBQO (0.1%) (Ex. 8) | Aqueous HCl (6N) | 1 | 30.5 | 58.2 |
| CRS | None | Aqueous HCl (4N) | 1 | 24.8 | |
| CRS | MQO (500 ppm) (Ex. 10) | Aqueous HCl (4N) | 1 | 4.18 | 83.2 |
| CRS | BQO (500 ppm) (Ex. 4) | Aqueous HCl (4N) | 1 | 5.75 | 76.8 |
| CRS | CBQO (500 ppm) | Aqueous HCl (4N) | 1 | 5.23 | 78.9 |

SS = stainless steel
CRS = cold rolled steel
BQO = benzyl quinolinium halide oligomer
CBQO = cross-linked benzyl p-α-quinolinium halide oligomer
MQO = methyl quinolimium sulfate oligomer

What is claimed is:

1. A composition of matter comprising a quaternized derivative of a quinoline oligomer, said derivative selected from compositions having the formula:

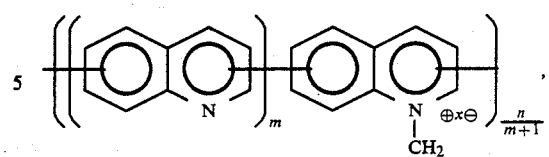

or

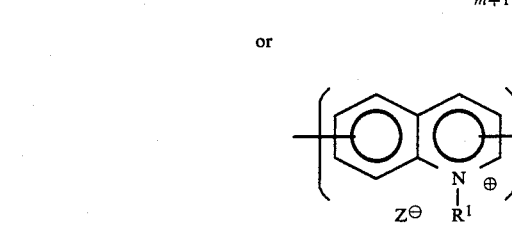

wherein n and m are integers, with n being greater than 2 and up to about 200 and m being equal to or greater than 1, R is H or an alkyl group having from 1 to about 20 carbon atoms, $R^1$ is an alkyl group having 1 to about 20 carbon atoms, $X^-$ is a chloride, bromide or iodide and $Z^-$ is an anion selected from $BF_4^-$, $SO_4^=$, $ClO_4^-$, $PF_6^-$ or $HSO_4^-$.

2. The composition of claim 1 wherein said derivative has the formula:

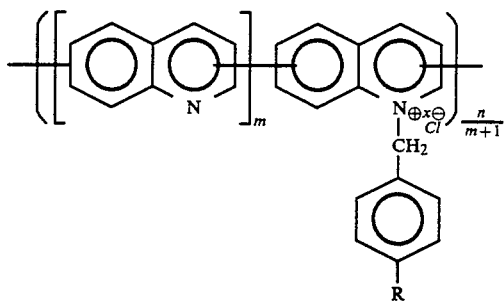

3. The composition of claim 1 wherein said derivative has the formula:

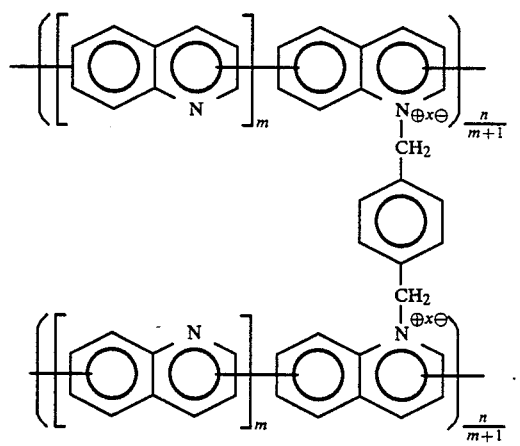

4. The composition of claim 1 wherein said derivative has the formula:

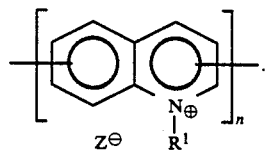

5. A method for forming a quaternary ammonium derivative of a quinoline oligomer or mixture thereof having the formula:

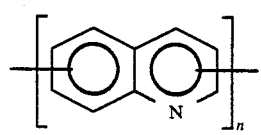

wherein n is from 2 to about 200 comprising contacting said oligomer at temperatures above about 25° C. to about 150° C. with an alkylating agent selected from the group consisting of:

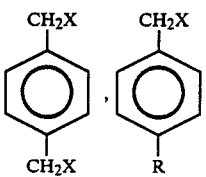, $(R^1O)_2SO_2$, $(R^1O)_2CHBF_4$, and $(R^1)_3OBF_4$.

wherein X is Cl, Br or I; R is H or an alkyl group of from 1 to about 20 carbon atoms and $R^1$ is an alkyl group of from 1 to about 20 carbon atoms, said contacting being for a time sufficient to form said quaternary ammonium derivative.

6. The method of claim 5 wherein said temperature is about 90° C.

7. The method of claim 6 wherein said contacting is conducted in an organic solvent.

8. The method of claim 7 wherein said alkylating agent is:

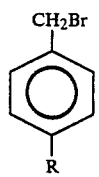

and is present in excess of said oligomer.

9. The method of claim 7 wherein said alkylating agent is:

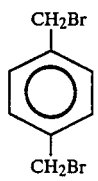

and said oligomer is present in excess of said alkylating agent.

10. The method of claim 7 wherein said alkylating agent is $(R^1O)_2SO_2$.

11. A composition for inhibiting the corrosion of metals in contact therewith comprising:
 a solvent; and,
 an effective amount of a quaternary ammonium salt or mixture thereof of the formula:

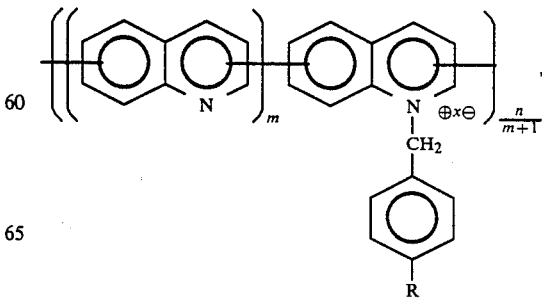

-continued

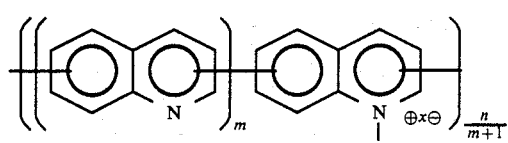

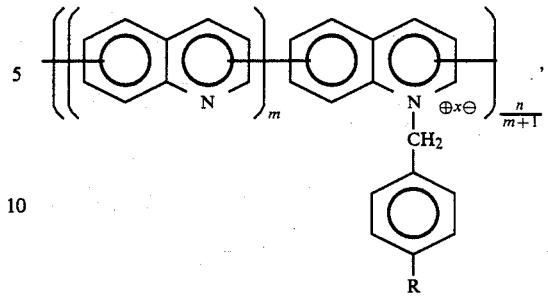

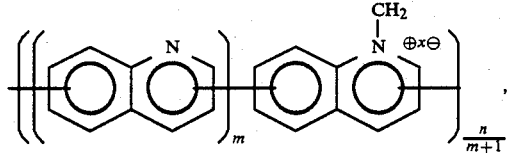

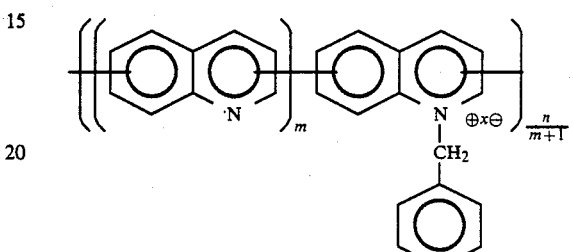

or

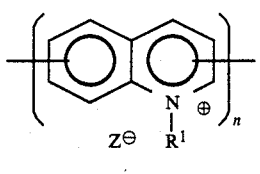

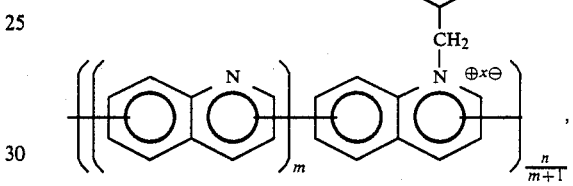

or

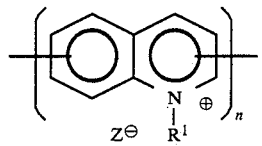

wherein n and m are integers, with n being greater than 2 and up to about 200 and m being equal to or greater than 1, R is H or an alkyl group having from 1 to about 20 carbon atoms, $R^1$ is an alkyl group having 1 to about 20 carbon atoms, $X^-$ is a chloride, bromide or iodide and $Z^-$ is an anion selected from $BF_4^-$, $SO_4^=$, $ClO_4^-$, $PF_6^-$ or $HSO_4^-$.

12. A process of inhibiting corrosion of metals comprising treating said metal with quaternized derivatives of a polyquinoline oligomer and mixtures thereof, said derivatives having the formula:

wherein n and m are integers, with n being greater than 2 and up to about 200 and m being equal to or greater than 1, R is H or an alkyl group having from 1 to about 20 carbon atoms, $X^-$ *is a chloride, bromide or iodide and $Z^-$* is an anion selected from $BF_4^-$, $SO_4^=$, $ClO_4^-$, $PF_6^-$ and $HSO_4^-$.

13. The composition of claim 11 wherein the solvent is water.

14. The composition of claim 13 wherein the quaternary ammonium salt or mixture thereof is present in amounts ranging from about 0.05 to about 2 weight percent based on the total weight of solution.

* * * * *